(12) United States Patent
Kasso

(10) Patent No.: US 7,762,006 B2
(45) Date of Patent: Jul. 27, 2010

(54) MEDICAL EQUIPMENT DRYING DEVICE

(75) Inventor: David Kasso, Camarillo, CA (US)

(73) Assignee: SiestaMed, Technologies, Ventura, CA (US)

( * ) Notice: Subject to any disclaimer, the term of this patent is extended or adjusted under 35 U.S.C. 154(b) by 385 days.

(21) Appl. No.: 11/818,800

(22) Filed: Jun. 14, 2007

(65) Prior Publication Data

US 2007/0289158 A1    Dec. 20, 2007

Related U.S. Application Data

(60) Provisional application No. 60/804,789, filed on Jun. 14, 2006.

(51) Int. Cl.
F26B 25/06 (2006.01)
(52) U.S. Cl. ............................. 34/90; 34/202; 34/211; 34/218; 128/26; 128/28; 600/2; 600/3
(58) Field of Classification Search ............... 34/90, 34/201, 202, 218; 128/26, 28; 600/2, 3
See application file for complete search history.

(56) References Cited

U.S. PATENT DOCUMENTS

| | | | | |
|---|---|---|---|---|
| 3,991,779 | A * | 11/1976 | Saurenman | 134/57 R |
| 5,203,343 | A * | 4/1993 | Axe et al. | 600/538 |
| 5,301,689 | A * | 4/1994 | Wennerholm | 128/848 |
| 5,687,714 | A * | 11/1997 | Kolobow et al. | 128/207.14 |
| 5,947,115 | A * | 9/1999 | Lordo et al. | 128/200.24 |
| 5,990,094 | A * | 11/1999 | Cole et al. | 514/47 |
| 6,006,748 | A * | 12/1999 | Hollis | 128/205.24 |
| 6,029,660 | A * | 2/2000 | Calluaud et al. | 128/203.12 |
| 6,086,585 | A * | 7/2000 | Hovda et al. | 606/45 |
| 6,091,973 | A * | 7/2000 | Colla et al. | 600/324 |
| 6,119,723 | A * | 9/2000 | Kenyon | 137/527 |
| 6,152,129 | A * | 11/2000 | Berthon-Jones | 128/200.24 |
| 6,155,986 | A * | 12/2000 | Brydon et al. | 600/538 |
| 6,159,208 | A * | 12/2000 | Hovda et al. | 606/41 |
| 6,182,657 | B1 * | 2/2001 | Brydon et al. | 128/205.24 |
| 6,203,542 | B1 * | 3/2001 | Ellsberry et al. | 606/41 |
| 6,213,119 | B1 * | 4/2001 | Brydon et al. | 128/204.23 |
| 6,237,592 | B1 * | 5/2001 | Surjadi et al. | 128/204.21 |
| 6,240,921 | B1 * | 6/2001 | Brydon et al. | 128/205.23 |
| 6,253,764 | B1 * | 7/2001 | Calluaud | 128/204.18 |
| 6,261,238 | B1 * | 7/2001 | Gavriely | 600/532 |
| 6,279,569 | B1 * | 8/2001 | Berthon-Jones | 128/200.24 |

(Continued)

FOREIGN PATENT DOCUMENTS

EP    0 329 171    * 8/1989

OTHER PUBLICATIONS

Company Catalog/Brochure: Mercury Medical®; "Dryers/Accessories"; pp. 116-117; Dated before May 22, 2007.

Primary Examiner—Stephen M. Gravini
(74) Attorney, Agent, or Firm—Cislo & Thomas, LLP

(57) ABSTRACT

A device and corresponding methods for drying medical equipment involving a dryer for drying the medical equipment; and a supply orb having a body and a cavity within the body for holding, ventilating, and storing the medical equipment, the at least one supply orb being mechanically coupled to the dryer for operation and being mechanically decoupled from the dryer during non-operation. The supply orb having a ventilation feature and a configuration conducive to creating a combined irrotational and rotational gas flow therein.

3 Claims, 2 Drawing Sheets

U.S. PATENT DOCUMENTS

| | | | | |
|---|---|---|---|---|
| 6,332,463 B1* | 12/2001 | Farrugia et al. | ........ | 128/204.18 |
| 6,336,454 B1* | 1/2002 | Farrell et al. | ........... | 128/200.24 |
| 6,363,270 B1* | 3/2002 | Colla et al. | ................. | 600/324 |
| 6,397,841 B1* | 6/2002 | Kenyon et al. | ......... | 128/202.27 |
| 6,432,103 B1* | 8/2002 | Ellsberry et al. | .............. | 606/41 |
| 6,435,180 B1* | 8/2002 | Hewson et al. | ......... | 128/204.18 |
| 6,526,974 B1* | 3/2003 | Brydon et al. | ......... | 128/205.24 |
| 6,532,957 B2* | 3/2003 | Berthon-Jones | ........ | 128/204.21 |
| 6,544,261 B2* | 4/2003 | Ellsberry et al. | .............. | 606/41 |
| 6,554,260 B1* | 4/2003 | Lipscombe et al. | ......... | 261/142 |
| 6,635,021 B1* | 10/2003 | Sullivan et al. | ............. | 600/529 |
| 6,688,307 B2* | 2/2004 | Berthon-Jones | ........ | 128/204.21 |
| 6,772,999 B2* | 8/2004 | Lipscombe et al. | ......... | 261/131 |
| 6,776,155 B2* | 8/2004 | Farrell et al. | ........... | 128/200.24 |
| 6,776,162 B2* | 8/2004 | Wood | .................. | 128/207.18 |
| 6,810,876 B2* | 11/2004 | Berthon-Jones | ........ | 128/204.21 |
| 6,949,262 B1* | 9/2005 | Smothers | .................... | 424/744 |
| 6,951,218 B2* | 10/2005 | Gradon et al. | ......... | 128/205.25 |
| 6,953,354 B2* | 10/2005 | Edirisuriya et al. | ......... | 439/191 |
| 6,997,177 B2* | 2/2006 | Wood | .................... | 128/200.24 |
| 7,004,908 B2* | 2/2006 | Sullivan et al. | ............. | 600/529 |
| 7,004,941 B2* | 2/2006 | Tvinnereim et al. | ........... | 606/41 |
| 7,090,672 B2* | 8/2006 | Underwood et al. | .......... | 606/41 |
| 7,131,969 B1* | 11/2006 | Hovda et al. | .................. | 606/45 |
| 7,137,389 B2* | 11/2006 | Berthon-Jones | ........ | 128/204.18 |
| 7,141,021 B2* | 11/2006 | Sullivan et al. | ............. | 600/529 |
| 7,178,524 B2* | 2/2007 | Noble | .................... | 128/206.11 |
| 7,233,938 B2* | 6/2007 | Carus et al. | ......................... | 1/1 |
| 7,237,770 B2* | 7/2007 | Lipscombe et al. | ......... | 261/142 |
| 7,285,090 B2* | 10/2007 | Stivoric et al. | .............. | 600/300 |
| 7,290,541 B2* | 11/2007 | Ivri et al. | ............... | 128/200.14 |
| 7,291,240 B2* | 11/2007 | Smith et al. | .................. | 156/195 |
| 7,302,950 B2* | 12/2007 | Berthon-Jones et al. | ............. | 128/204.23 |
| 7,306,205 B2* | 12/2007 | Huddart et al. | ............... | 261/130 |
| 7,309,687 B1* | 12/2007 | Brines et al. | ..................... | 514/2 |
| 7,314,046 B2* | 1/2008 | Schroeder et al. | ....... | 128/200.14 |
| 7,326,721 B2* | 2/2008 | Edgar et al. | .................. | 514/320 |
| 7,422,759 B2* | 9/2008 | Kepner et al. | ................ | 424/618 |
| 7,468,116 B2* | 12/2008 | Smith et al. | .................. | 156/344 |
| 7,482,460 B2* | 1/2009 | Edgar et al. | .................. | 546/196 |
| 7,491,200 B2* | 2/2009 | Underwood | .................. | 606/41 |
| 7,494,998 B2* | 2/2009 | Coughlin et al. | ........ | 514/254.02 |
| 7,516,743 B2* | 4/2009 | Hoffman | ................ | 128/204.23 |
| 7,524,864 B2* | 4/2009 | Edgar et al. | .................. | 514/320 |
| 7,530,403 B2* | 5/2009 | Cano | ........................... | 169/24 |
| 7,563,785 B2* | 7/2009 | Edgar et al. | ............. | 514/211.13 |
| 7,592,333 B2* | 9/2009 | Edgar et al. | ............. | 514/211.13 |
| 7,640,055 B2* | 12/2009 | Geva et al. | ................... | 600/544 |
| 2003/0000527 A1* | 1/2003 | Stenzler et al. | ........ | 128/204.18 |
| 2003/0132535 A1* | 7/2003 | Lipscombe et al. | ......... | 261/142 |
| 2003/0236015 A1* | 12/2003 | Edirisuriya et al. | ......... | 439/191 |
| 2004/0226560 A1* | 11/2004 | Lipscombe et al. | .... | 128/204.17 |
| 2005/0224236 A1* | 10/2005 | Cano | ........................... | 169/24 |
| 2006/0137886 A1* | 6/2006 | Cano | ........................... | 169/24 |
| 2007/0163600 A1* | 7/2007 | Hoffman | ................ | 128/207.18 |
| 2007/0246045 A1* | 10/2007 | Hoffman | ................ | 128/204.18 |
| 2007/0289158 A1* | 12/2007 | Kasso | ......................... | 34/201 |
| 2008/0047560 A1* | 2/2008 | Veliss et al. | ............ | 128/206.24 |
| 2008/0127978 A1* | 6/2008 | Rubin et al. | ........... | 128/204.23 |
| 2008/0190427 A1* | 8/2008 | Payton et al. | .......... | 128/203.27 |
| 2009/0014008 A1* | 1/2009 | Takishita et al. | ....... | 128/207.11 |
| 2009/0218108 A1* | 9/2009 | Cano | ........................... | 169/24 |
| 2009/0223518 A1* | 9/2009 | Kwok et al. | ........... | 128/205.25 |

\* cited by examiner

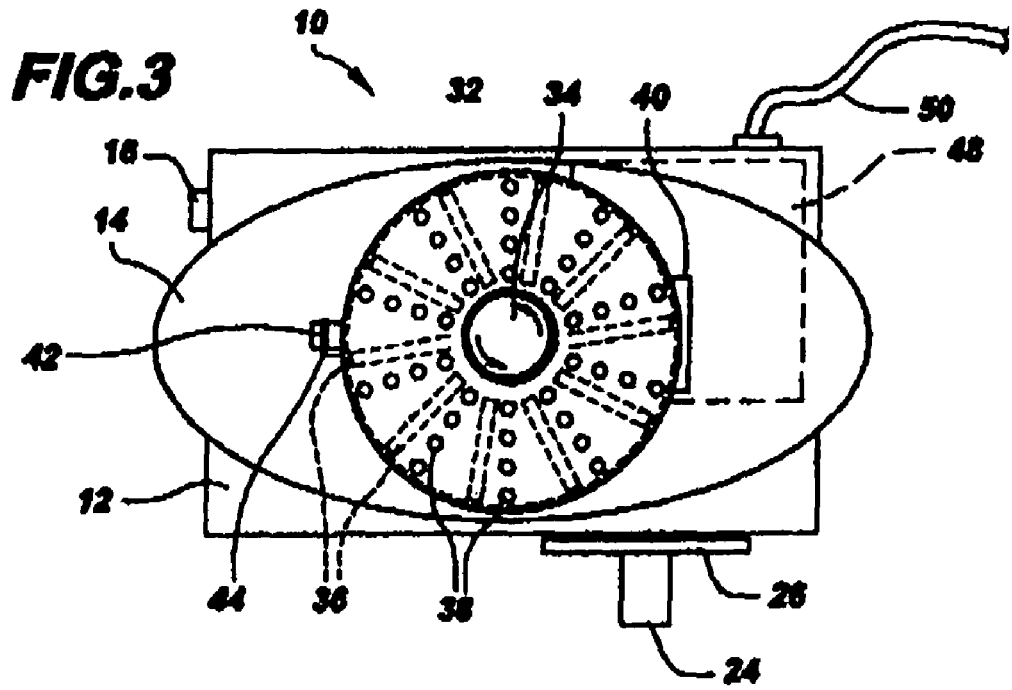
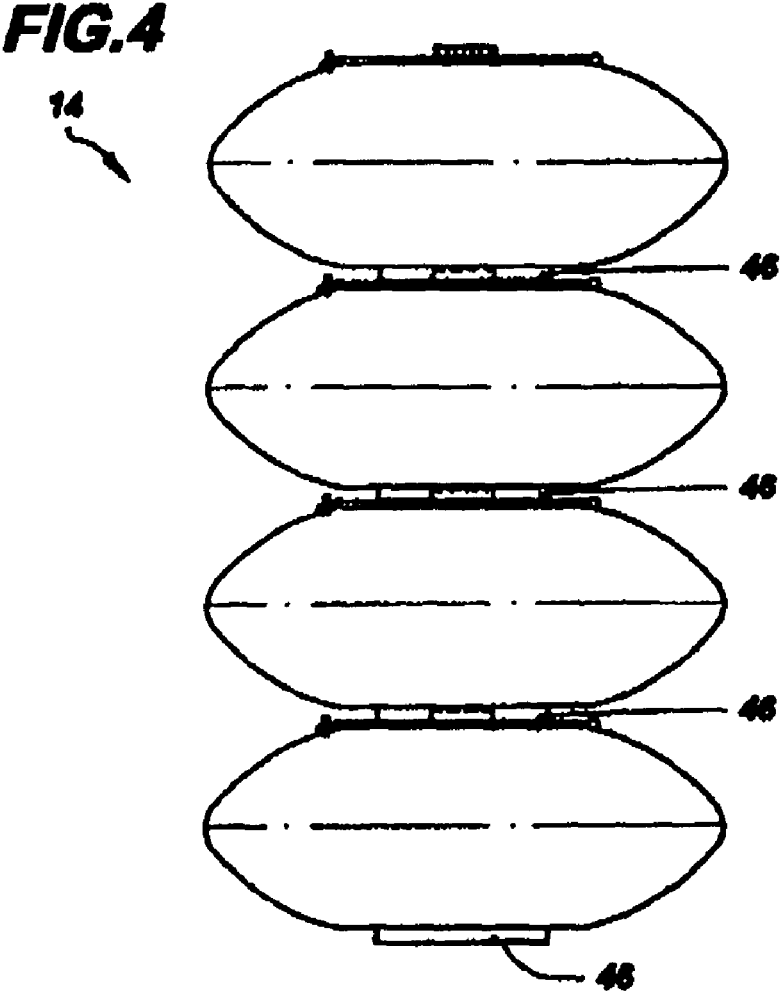

MEDICAL EQUIPMENT DRYING DEVICE

CROSS-REFERENCE TO RELATED APPLICATION(S)

This document is a non-provisional patent application, which is related to, and claims priority from, U.S. Provisional Patent Application Ser. No. 60/804,789, entitled "Hurricane CPAP Equipment Drying Device," filed on Jun. 14, 2006, the disclosure of which is hereby incorporated in its entirety by reference.

TECHNICAL FIELD

The present invention technically relates to devices and methods for cleaning and drying medical equipment. More particularly, the present invention technically relates to devices and methods for cleaning and drying respiratory equipment. Even more particularly, the present invention technically relates to devices and methods for cleaning and sleep apnea equipment.

BACKGROUND ART

The currently existing related art involves several apparatuses and methods for cleaning and drying medical equipment, such as respiratory equipment and accessories, e.g., masks, masks having nasal interfaces, masks having nasal prongs, and full face masks, filters, and CPAP humidifiers. As background, "Continuous Positive Airway Pressure" (CPAP) is an effective treatment for a condition known as "obstructive sleep apnea," chronic snoring, and other sleep disorders in the related art. CPAP therapy is applied during sleep, wherein a patient wears a facemask which is in gaseous communication with a pump, e.g., a "CPAP" or "CPAP machine," as known in the medical field. The pump forces air into the nasal passages of the patient at pressures high enough to overcome any obstructions in the airway, thereby stimulating normal breathing. The pressure, which is delivered into an upper airway, is continuous during both inspiration as well as expiration.

Further, because the airflow from the CPAP machine is delivered through a mask that fits on the face and covers either both the nose and the mouth or just the nose, such masks are typically cleaned and dried to prevent the growth of unwanted organisms which tend to culture in the presence of moisture. This circumstance can lead to infection of the patient's respiratory tract if the CPAP equipment is not properly cleaned and dried. The oils from the patient's skin and the minerals in tap water can cause premature breakdown in the CPAP equipment as well as creating an environment conducive to bacterial growth, especially in the mask. Typically, the CPAP equipment is merely dried by hanging the equipment in the open air away from direct sunlight to minimize the possibility of UV-degradation of the materials.

However, the common problem with the foregoing related art apparatuses and methods is that they require too much time to dry the CPAP equipment and do not dry the equipment thoroughly. In addition, open-air drying may introduce yet new organisms, e.g., those that are air-born onto and into the slowly drying equipment. Thus, a long-felt need is seen to exist for a device and a method for drying CPAP equipment which decreases the drying time as well as increases the drying effectiveness.

DISCLOSURE OF THE INVENTION

The present invention addresses the foregoing problems in the related art in a device and corresponding methods for quickly drying medical equipment, e.g., CPAP equipment, by example only. The present invention device generally comprises: a dryer, having an on/off switch, a digital display, and an adjustable timer for providing automatic shut-off, and at least one supply orb for holding at least one piece of equipment being dried by using a continuous flow of warm or hot air. The dryer and the orb are coupled together for use and may be decoupled when not in use. The at least one supply orb is stackable for convenient storage, such as would be useful in an institution that uses multiple sets of CPAP equipment. Further, the present invention device can be used by users, such as patients in their homes for their personal CPAP equipment drying, by medical personnel in a sleep laboratory, or by medical personnel in a hospital for their drying CPAP equipment as well as any other reusable testing supply inventory. The bowl or supply orb can comprise a small volume for personal use or a large volume for institutional use. The orb comprises a configuration conducive to therein generating at least one gas flow, such as at least one irrotational flow and at least one rotational flow, i.e., at least one gaseous vortex, for facilitating drying of the medical equipment.

The present invention also involves a method of fabricating a drying device, the method generally comprising the steps of: providing a dryer, the dryer providing step comprising providing an on/off switch, providing a digital display, and providing an adjustable timer for providing automatic shut-off; and providing at least one supply orb for holding at least one piece of equipment being dried by using a continuous flow of warm or hot air. The dryer providing step and the at least one orb providing step, together, comprising providing the dryer and the at least one orb being capable of coupling for use and decoupling when not in use. The at least one supply orb providing step comprising providing the at least one supply orb being stackable for convenient storage, such as would be useful in an institution that uses multiple sets of CPAP equipment. The bowl or supply orb providing step further comprises providing the at least one supply orb in a small volume for personal use or in a large volume for institutional use.

The present invention also involves a corresponding method of drying CPAP equipment by way of a drying device, the method generally comprising the steps of: providing a dryer device, the dryer device providing step comprising providing a dryer, the dryer providing step comprising providing an on/off switch, providing a digital display, and providing an adjustable timer for providing automatic shut-off; and providing at least one supply orb for holding at least one piece of equipment being dried by using a continuous flow of warm or hot air. The dryer providing step and the at least one orb providing step, together, comprising providing the dryer and the at least one orb being capable of coupling for use and decoupling when not in use. The at least one supply orb providing step comprising providing the at least one supply orb being stackable for convenient storage, such as would be useful in an institution that uses multiple sets of CPAP equipment. The bowl or supply orb providing step further comprises providing the at least one supply orb in a small volume for personal use or in a large volume for institutional use. Further, the present method further comprises the step of placing the CPAP equipment in the at least one orb by at least one user, such a patient at home for drying personal CPAP equipment, medical personnel in a sleep laboratory, or medical personnel in a hospital for their drying CPAP equipment as well as any other reusable testing supply inventory.

Advantages of the present invention include, but are not limited to, providing a safe, convenient, and fast device and corresponding methods, for drying CPAP equipment and related accessories, and providing an option for storing a plurality of devices for handy institutional use. Other features of the present invention are disclosed, or are apparent, in the section entitled "Mode(s) for Carrying-Out the Invention," disclosed, infra.

BRIEF DESCRIPTION OF THE DRAWING(S)

For a better understanding of the present invention, reference is made to the below-referenced accompanying Drawing(s). Reference numbers refer to the same or equivalent parts of the present invention throughout the several figures of the Drawing(s).

FIG. 3 is a top plan view of a device for drying medical equipment, in accordance with the present invention.

FIG. 4 is a side elevation view a plurality of supply orbs of a device for drying medical equipment, the orbs being stackable for facilitating storage in an institutional setting, such as a hospital, a sleep laboratory, or a sleep clinic, in accordance with the present invention.

MODE(S) FOR CARRYING OUT THE INVENTION

Figure 1:
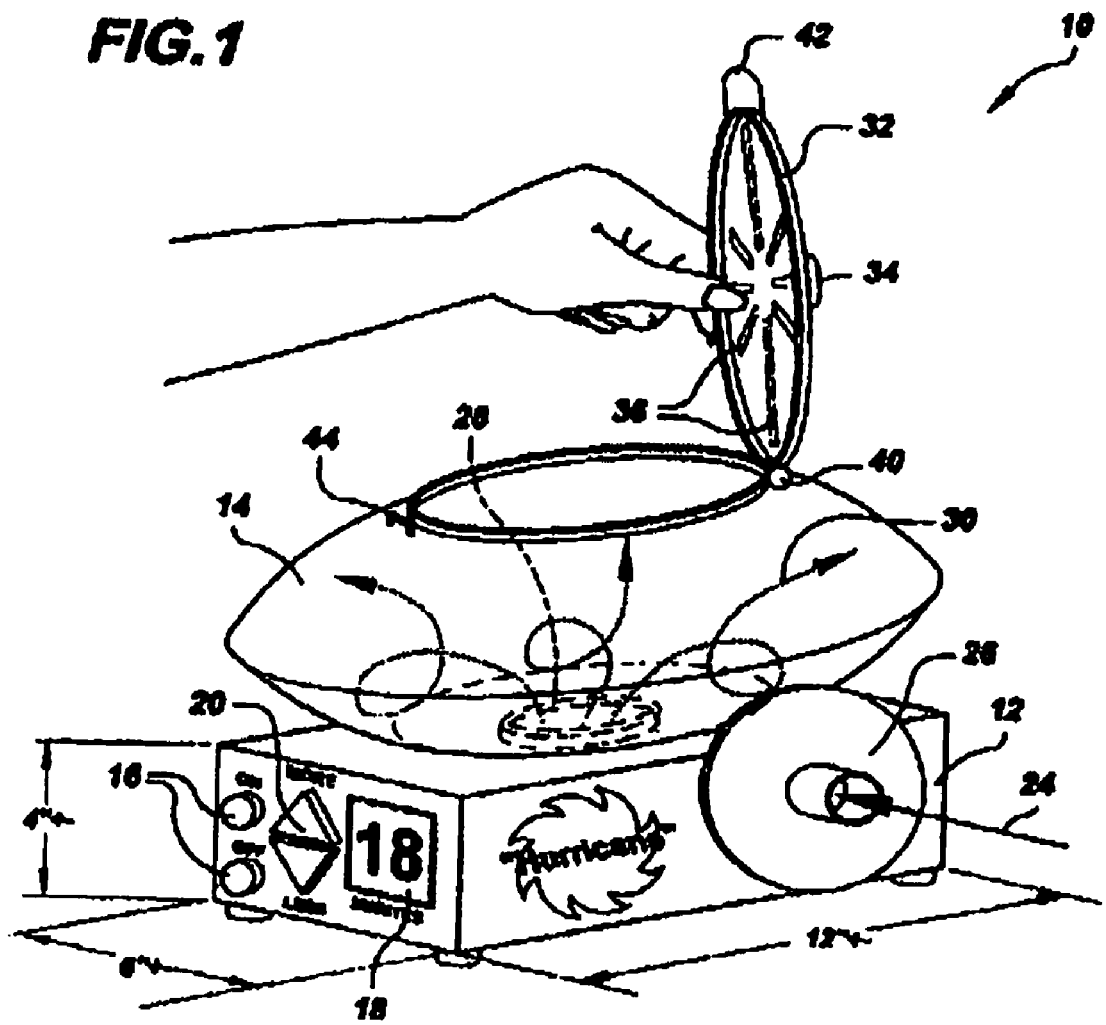
FIG. 1 is a perspective view of a device for drying medical equipment, in accordance with the present invention.

FIG. 1 illustrates, in a perspective view, a drying device 10 for drying medical equipment, such as CPAP equipment by example only, in accordance with the present invention. The drying device 10 generally comprises two main components, the first component being a dryer 12, the dryer 12 comprising an automatic and time-adjustable filtered drying mechanism of any suitable size and type for accommodating the second component; and the second component being at least one supply orb 14 which holds the medical equipment or supplies that are receiving the continuous warm/hot vertical air for drying. These two components are coupled together for use and may be decoupled when not in use.

Still referring to FIG. 1, the drying device 10 is used to quickly and efficiently to dry presoaked, cleansed, and rinsed medical equipment, such as CPAP equipment, e.g., a mask, headgear, tubing, and related equipment, by ventilating the equipment under at least one condition such as at least one irrotational gas flow, wherein the curl of the velocity vector equals zero, and at least one rotational gas flow, wherein the curl of the velocity vector for the air flow is greater than zero, i.e., a combination of a laminar flow with at least one gaseous vortex, within at least one supply orb 14. The supply orb 14 comprises a polymeric material, such as plastic and a composite, and a small volume for in-home use or a large volume for institutional use. The supply orb 14 also comprises a lid 32 having a ventilation feature. The device 10 further comprises a removable filter 26, wherein incoming air is filtered through the removable filter 26 and into the dryer 12. The filtered air is heated, whereby filtered warm/hot air 30 is provided. The filtered warm/hot air 30 is continuously passed through the ventilation feature for a short duration of time, such duration of time being controlled by an automatic shut-off timer 20. Users of the drying device 10 include patients at home for drying their personal CPAP equipment, medical personnel in a sleep laboratory for drying reusable testing supply inventory, and medical personnel in a hospital for drying reusable testing supply inventory.

Also referring to FIG. 1, the automatic and time-adjustable filtered drying mechanism in the dryer 12 comprises a heating base of any suitable size and type. The supply orb 14 holds the medical equipment or medical supplies that are receiving the continuous warm/hot air for drying. The supply orb 14 comprises any size for containing the equipment or supplies, wherein the supply orb 14 also stores the equipment or supplies for later use. The dryer 12 further comprises at least one feature, such as an automatic on/off switch 16, a digital time display 18, and an adjustable timer 20. The supply orb 14 comprises a cavity 22 for retaining the CPAP equipment to be dried and/or stored. The removable air filter 26, through which airflow 24 passes, removes bacteria therefrom. The supply orb 14 comprises an air hole 28 (inlet) disposed through its lower surface and through which heated filtered air flow 30 passes, as well as a lid 32 for accessing the cavity 22. As discussed, supra, the lid 32 comprises a ventilation feature (outlet), the ventilation feature including a plurality of ventilation holes 38 disposed on an outer portion of the lid 32, a plurality of ventilation slots 36 disposed on an inner portion of the lid 32, and a knob 34 for adjusting the ventilation by rotating the inner portion in relation to outer portion. The supply orb 14 further comprises a hinge 40 for mechanically coupling the lid 32 to a body of the orb 14, a locking feature for locking the lid 32 onto the body of the orb 14, the locking feature comprising a sliding tab 42 and a locking guide 44 for providing an interference-fit to the sliding tab 42. The dryer 12 further comprises a motor 48 for driving the air flow 24 through the orb 14 and power source, wherein the power source comprises at least one source such as power supplied via a wall outlet through a power supply cord 50 and any portable power supply, e.g., batteries or rechargeable batteries.

Figure 2:
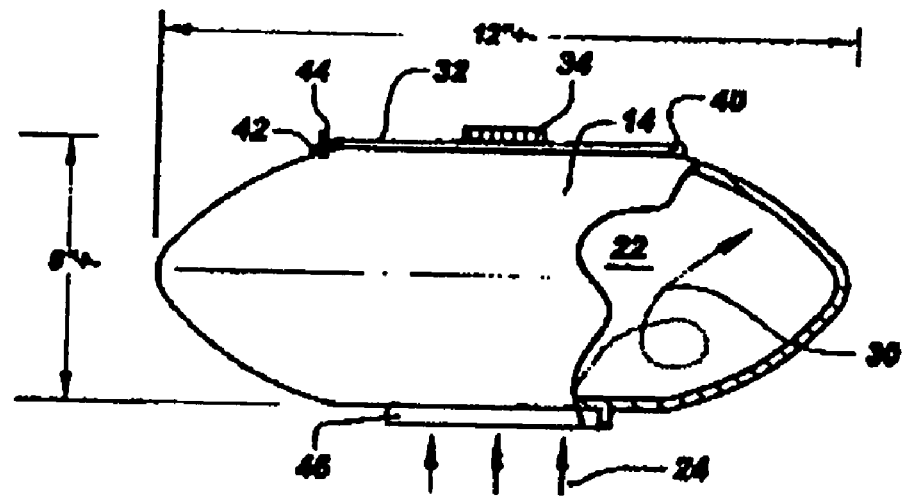
FIG. 2 is a side elevation view of a supply orb with a partial cut-away section of a device for drying medical equipment, in accordance with the present invention.

FIG. 2 illustrates, in a side elevation view, a supply orb 14 of a drying device 10 with a partial cut-away section, in accordance with the present invention. The supply orb 14 comprises a polymeric material such as a plastic and a composite. The connector ring 46 facilitates manually pushing the orb 14 onto the dryer 12 by the user. The connector ring 46 comprises a configuration which complements that of the lid 32 for facilitating stacking of the orbs 14, wherein the knob 34 of one orb 14 concentrically nests within the connector ring 46 of another orb 14, and wherein the connecter ring 46 on one orb 14 concentrically nests within a perimeter of the lid 32 of another orb 14, for facilitating stacking.

FIG. 3 illustrates, in a top plan view, a drying device, in accordance with the present invention. The supply orb 14 comprises an air hole 28 (inlet) disposed on its lower surface, through which heated filtered air flow 30 passes, and a lid 32 for accessing the cavity 22. The lid 32 comprises a ventilation feature (outlet) which includes a plurality of ventilation holes 38 disposed on an outer portion of the lid 32, a plurality of ventilation slots 36 disposed on an inner portion of the lid 32, and a knob 34 for adjusting the ventilation by rotating the inner portion in relation to outer portion.

FIG. 4 illustrates, in a side elevation view, a plurality of supply orbs 14 being stackable for facilitating storage in an institutional setting, in accordance with the present invention. The lower surface of each orb 14 comprises a configuration that complements that of the lid 32 for facilitating stacking.

The present invention also involves a method $M_1$ of fabricating a drying device 10, the method $M_1$ generally comprising the steps of: providing a dryer 12, the dryer 12 providing step comprising providing an on/off switch 16, providing a digital time display 18, and providing an adjustable timer 20 for providing automatic shut-off; and providing at least one supply orb 14 for holding at least one piece of equipment (not shown) being dried by using a continuous flow of warm or hot air. The dryer 12 providing step and the at least one orb 14 providing step, together, comprising providing the dryer 12 and the at least one orb 14 being capable of coupling for use and decoupling when not in use. The at least one supply orb 14 providing step comprising providing the at least one supply orb 14 being stackable for convenient storage, such as would be useful in an institution that uses multiple sets of CPAP equipment. The supply orb 14 providing step further comprises providing the at least one supply orb 14 in a small volume for personal use or in a large volume for institutional use.

The present invention also involves a corresponding method $M_2$ of drying CPAP equipment by way of a drying device 10, the method $M_2$ generally comprising the steps of: providing a dryer device 10, the drying device 10 providing step comprising providing a dryer 12, the dryer 12 providing step comprising providing an on/off switch 16, providing a digital time display 18, and providing an adjustable timer 20 for providing automatic shut-off; and providing at least one supply orb 14 for holding at least one piece of equipment being dried by using a continuous flow of warm or hot air. The dryer 12 providing step and the at least one orb providing step, together, comprising providing the dryer 12 and the at least one orb 14 being capable of coupling for use and decoupling when not in use. The at least one supply orb 14 providing step comprising providing the at least one supply orb 14 being stackable for convenient storage, such as would be useful in an institution that uses multiple sets of CPAP equipment. The supply orb 14 providing step further comprises providing the at least one supply orb 14 in a small volume for personal use or in a large volume for institutional use. Further, the present method $M_2$ further comprises the step of placing the medical equipment or supplies, e.g., CPAP equipment, in the at least one orb 14 by at least one user, such as a patient at home, by medical personnel at a sleep laboratory, or by medical personnel at a hospital, for their drying CPAP equipment as well as any other reusable testing supply inventory. The method $M_2$ further comprises adjusting the drying time duration using the adjustable timer 20, adjusting the ventilation by using the knob 34, and switching "on" the device using the switch 16, thereby drying the equipment. The method $M_2$ further comprises at least one of the following steps: removing the dried equipment, storing the dried equipment in the orb 14, and stacking a plurality of orbs 14.

Information as herein shown and described in detail is fully capable of attaining the above-described object of the invention, the presently preferred embodiment of the invention, and is, thus, representative of the subject matter being broadly contemplated by the present invention. The scope of the present invention fully encompasses other embodiments which may become obvious to those skilled in the art, and is to be limited, accordingly, by nothing other than the appended claims, wherein reference to an element in the singular is not intended to mean "one and only one" unless explicitly so stated, but rather "one or more." All structural and functional equivalents to the elements of the above described preferred embodiment and additional embodiments that are known to those of ordinary skill in the art are hereby expressly incorporated by reference and are intended to be encompassed by the present claims.

Moreover, no requirement exists for a device or method to address each and every problem sought to be resolved by the present invention, for such to be encompassed by the present claims. Furthermore, no element, component, or method step in the present disclosure is intended to be dedicated to the public regardless of whether the element, component, or method step is explicitly recited in the claims. However, various changes and modifications in form, material, and fabrication material detail may be made without departing from the spirit and scope of the inventions as set forth in the appended claims should be readily apparent to those of ordinary skill in the art. No claim herein is to be construed under the provisions of 35 U.S.C. §112, sixth paragraph, unless the element is expressly recited using the phrase "means for."

INDUSTRIAL APPLICABILITY

The present invention industrially applies to devices and methods for cleaning and drying medical equipment. More particularly, the present invention industrially applies to devices and methods for cleaning and drying respiratory equipment. Even more particularly, the present invention industrially applies to devices and methods for cleaning and sleep apnea equipment.

What is claimed:

1. A device for drying medical equipment, comprising:
   a dryer for drying the medical equipment;
   at least one supply orb having a body and a cavity within the body for holding, ventilating, and storing the medical equipment, the at least one supply orb being mechanically coupled to the dryer for operation and being mechanically decoupled from the dryer during non-operation; and
   a removable filter being mechanically coupled to the dryer for filtering bacteria from incoming air,
   wherein the dryer comprises:
      a base; and
      a drying mechanism disposed in the base, the drying mechanism comprising a motor, a heater, and a blower,
   wherein the medical equipment comprises CPAP presoaked, cleansed, and rinsed CPAP equipment,
   wherein the CPAP equipment comprises at least one element selected from a group consisting essentially of a mask, headgear, tubing, and a CPAP accessory,
   wherein the at least one supply orb comprises at least one polymeric material selected from a group consisting essentially of a plastic and a composite,
   wherein the at least one supply orb comprises a volume selected from a group consisting essentially of a small volume for in-home use and a large volume for institutional use,
   wherein the at least one supply orb comprises:
      an inlet air hole disposed on its lower surface, through which heated filtered air flow passes; and
      a lid, having an outer portion and an inner portion, for accessing the cavity, the lid comprising a ventilation feature, the ventilation feature including a plurality of ventilation holes disposed through the outer portion, a plurality of ventilation slots disposed through the inner portion, and a knob, being disposed through the outer portion and being mechanically coupled to the inner portion, for adjusting the ventilation by rotating the inner portion in relation to the outer portion, wherein the supply orb further comprises:
  a hinge for mechanically coupling the lid to the body; and
  a locking feature for locking the lid onto the body, the locking feature comprising a sliding tab and a locking guide for providing an interference-fit to the sliding tab,
wherein the dryer comprises:
  a motor for driving the air through the orb; and
  a power source, wherein the power source comprises at least one source selected from a group consisting essentially of power supplied via a wall outlet through a power supply cord and any portable power supply,
wherein the portable power supply comprises at least one source selected from a group consisting essentially of at least one battery and at least one rechargeable battery,
wherein the removable filter filters the air,
wherein the filtered air is heated by the dryer, and
wherein the heated filtered air is continuously blown on the medical equipment disposed in the at least one supply orb and through the ventilation feature for a short duration of time, the short duration of time being controllable by an adjustable timer,
wherein the supply orb comprises a connector ring for facilitating manually pushing the at least one supply orb onto the dryer by the user,
wherein the at least one supply orb comprises a plurality of supply orbs being stackable for facilitating storage in an institutional setting, and
wherein a lower surface of each supply orb comprises a configuration, which complements that of the lid for facilitating stacking.

2. A device for drying medical equipment, comprising:
a dryer for drying the medical equipment;
at least one supply orb having a body and a cavity within the body, the at least one supply orb being detachably coupled to the dryer; and
a removable filter being mechanically coupled to the dryer,
  wherein the dryer comprises:
    a base; and
    a drying mechanism disposed in the base, the drying mechanism comprising a motor, a heater, and a blower, wherein the medical equipment comprises CPAP presoaked, cleansed, and rinsed CPAP equipment, wherein the CPAP equipment comprises at least one element selected from a group consisting essentially of a mask, headgear, tubing, and a CPAP accessory, wherein the at least one supply orb comprises at least one polymeric material selected from a group consisting essentially of a plastic and a composite, wherein the at least one supply orb comprises a volume selected from a group consisting essentially of a small volume for in-home use and a large volume for institutional use,
  wherein the at least one supply orb comprises:
    an inlet air hole disposed on its lower surface, through which filtered air flow passes; and
    a lid, having an outer portion and an inner portion, for accessing the cavity, the lid comprising a ventilation feature, the ventilation feature including a plurality of ventilation holes disposed through the outer portion, a plurality of ventilation slots disposed through the inner portion, and a knob, being disposed through the outer portion and being mechanically coupled to the inner portion, for adjusting the ventilation by rotating the inner portion in relation to the outer portion,
  wherein the supply orb further comprises:
    a hinge for mechanically coupling the lid to the body; and
    a locking feature for locking the lid onto the body, the locking feature comprising a sliding tab and a locking guide for providing an interference-fit to the sliding tab, wherein the dryer further comprises a power source, wherein the power source comprises at least one source selected from a group consisting essentially of power supplied via a wall outlet through a power supply cord and a portable power supply,
  wherein the removable filter filters the air,
  wherein the filtered air is heated by the dryer, and
  wherein the heated filtered air is continuously blown on the medical equipment disposed in the at least one supply orb and through the ventilation feature for a short duration of time, the short duration of time being controllable by an adjustable timer,
  wherein the supply orb comprises a connector ring for facilitating manually pushing the at least one supply orb onto the dryer,
  wherein the at least one supply orb comprises a plurality of supply orbs being stackable for facilitating storage, and
  wherein a lower surface of each supply orb comprises a configuration, which complements that of the lid for facilitating stacking.

3. A device for drying medical equipment, comprising:
a dryer for drying the medical equipment;
at least one supply orb having a body and a cavity within the body, the at least one supply orb being detachably coupled to the dryer; and
a removable filter being mechanically coupled to the dryer,
  wherein the dryer comprises:
    a base; and
    a drying mechanism disposed in the base, the drying mechanism comprising a motor, a heater, and a blower, wherein the medical equipment comprises CPAP presoaked, cleansed, and rinsed CPAP equipment, wherein the at least one supply orb comprises at least one polymeric material selected from a group consisting essentially of a plastic and a composite, wherein the at least one supply orb comprises a volume selected from a group consisting essentially of a small volume for in-home use and a large volume for institutional use,
  wherein the at least one supply orb comprises:
    an inlet air hole disposed on its lower surface, through which filtered air flow passes; and
    a lid, having an outer portion and an inner portion, for accessing the cavity, the lid comprising a ventilation feature, the ventilation feature including a plurality of ventilation holes disposed through the outer portion, a plurality of ventilation slots disposed through the inner portion, and a knob, being disposed through the outer portion and being mechanically coupled to the inner portion, for adjusting the ventilation by rotating the inner portion in relation to the outer portion,
  wherein the supply orb further comprises:
    a hinge for mechanically coupling the lid to the body; and
    a locking feature for locking the lid onto the body, the locking feature comprising a sliding tab and a locking guide for providing an interference-fit to the sliding tab, wherein the dryer further comprises a power source, wherein the power source comprises at least one source selected from a group consisting essentially of power supplied via a wall outlet through a power supply cord and a portable power supply,
wherein the removable filter filters the air,
wherein the filtered air is heated by the dryer, and
wherein the heated filtered air is blown on the medical equipment disposed in the at least one supply orb and through the ventilation feature for a short duration of time, the short duration of time being controllable by an adjustable timer,
wherein the supply orb comprises a connector ring for facilitating manually pushing the at least one supply orb onto the dryer,
wherein a lower surface of each supply orb comprises a configuration, which complements that of the lid for facilitating stacking with additional supply orbs.

* * * * *